US00PP32513P2

(12) United States Plant Patent
Mathey

(10) Patent No.: US PP32,513 P2
(45) Date of Patent: Nov. 24, 2020

(54) ***HYDRANGEA* PLANT NAMED 'SMNHPM'**

(50) Latin Name: *Hydrangea paniculata*
Varietal Denomination: SMNHPM

(71) Applicant: Spring Meadow Nursery, Inc., Grand Haven, MI (US)

(72) Inventor: Megan M Mathey, Holland, MI (US)

(73) Assignee: Spring Meadow Nursey, Inc., Grand Haven, MI (US)

( * ) Notice: Subject to any disclaimer, the term of this patent is extended or adjusted under 35 U.S.C. 154(b) by 0 days.

(21) Appl. No.: 16/602,601

(22) Filed: Nov. 4, 2019

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 5/02; A01H 5/00
See application file for complete search history.

*Primary Examiner* — Kent L Bell
(74) *Attorney, Agent, or Firm* — Cassandra Bright

(57) ABSTRACT

A new and distinct *Hydrangea* cultivar named 'SMNHPM' is disclosed, characterized by exceptionally large panicles and strong stems. Flowers are white with an intense pink flush, turning intense pink with maturity. The new variety is a *Hydrangea*, normally produced as an ornamental plant.

3 Drawing Sheets

Latin name of the genus and species: *Hydrangea paniculata.*

Variety denomination: 'SMNHPM'.

BACKGROUND OF THE INVENTION

The new *Hydrangea* cultivar is a product of a planned breeding program conducted by the inventor, at a commercial nursery in Grand Haven, Mich. The objective of the breeding program was to produce new colors and forms of *Hydrangea paniculata*. The cross resulting in this new variety was made during the Summer of 2013.

The seed parent is the variety *Hydrangea paniculata* 'Firelight', U.S. Plant Pat. No. 25,135. The pollen parent is the unpatented variety *Hydrangea paniculata* 'Red Pink'. The new variety was identified as a potentially interesting selection in the Summer of 2016 at a commercial greenhouse in Grand Haven, Mich. Date of first sale was Jun. 25, 2019, occurring in the United States. This sale was made directly by the inventor or one who obtained the claimed invention directly or indirectly from the inventor. This sale and all public disclosures made between Jun. 25, 2019 and the filing of this application fall within the exception allowed under 102(b)(1).

Asexual reproduction of the new cultivar 'SMNHPM' by vegetative softwood cuttings was first performed during the Summer of 2016, at a commercial greenhouse in Grand Haven, Mich. Subsequent asexual propagation has shown that the unique features of this cultivar are stable and reproduced true to type in 3 successive generations.

SUMMARY OF THE INVENTION

The cultivar 'SMNHPM' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMNHPM' These characteristics in combination distinguish 'SMNHPM' as a new and distinct *Hydrangea* cultivar:

1. Exceptionally large panicles.
2. White flowers with an intense pink flush, turning overall intense pink.
3. Strong stems.

PARENT COMPARISON

Plants of the new cultivar 'SMNHPM' are similar to plants of the seed parent in most horticultural characteristics, however, plants of the new cultivar 'SMNHPM' differ in the following;

1. The new variety has lighter pink with green late Summer/Fall flower color; the seed parent has red-pink late Summer/Fall color.
2. The new variety has lighter green foliage than the seed parent.
3. The new variety has wider flower panicles than the seed parent.
4. The new variety has narrower sepals than the seed parent.

Plants of the new cultivar 'SMNHPM' are similar to plants of the pollen parent in most horticultural characteristics, however, plants of the new cultivar 'SMNHPM' differ in the following;

1. The new variety has lighter pink with green late Summer/Fall flower color; the pollen parent has a much more red late Summer/Fall color.
2. The new variety has larger flower panicles than the seed parent.

COMMERCIAL COMPARISON

Plants of the new cultivar 'SMNHPM' can be compared to the variety *Hydrangea paniculata* 'SMHPLQF', U.S.

Plant Pat. No. 25,136. These varieties are similar in most horticultural characteristics; however 'SMNHPM' differs in the following:

1. The new variety is a mophead, while this comparator is a lacecap.
2. The new variety has darker green leaves than this comparator.
3. The new variety has darker pink flowers than this comparator.

BRIEF DESCRIPTION OF THE PHOTOGRAPHS

The accompanying photograph in FIG. 1 illustrates in full color a typical plant of 'SMNHPM' with inflorescences beginning to mature.

Figure 1:
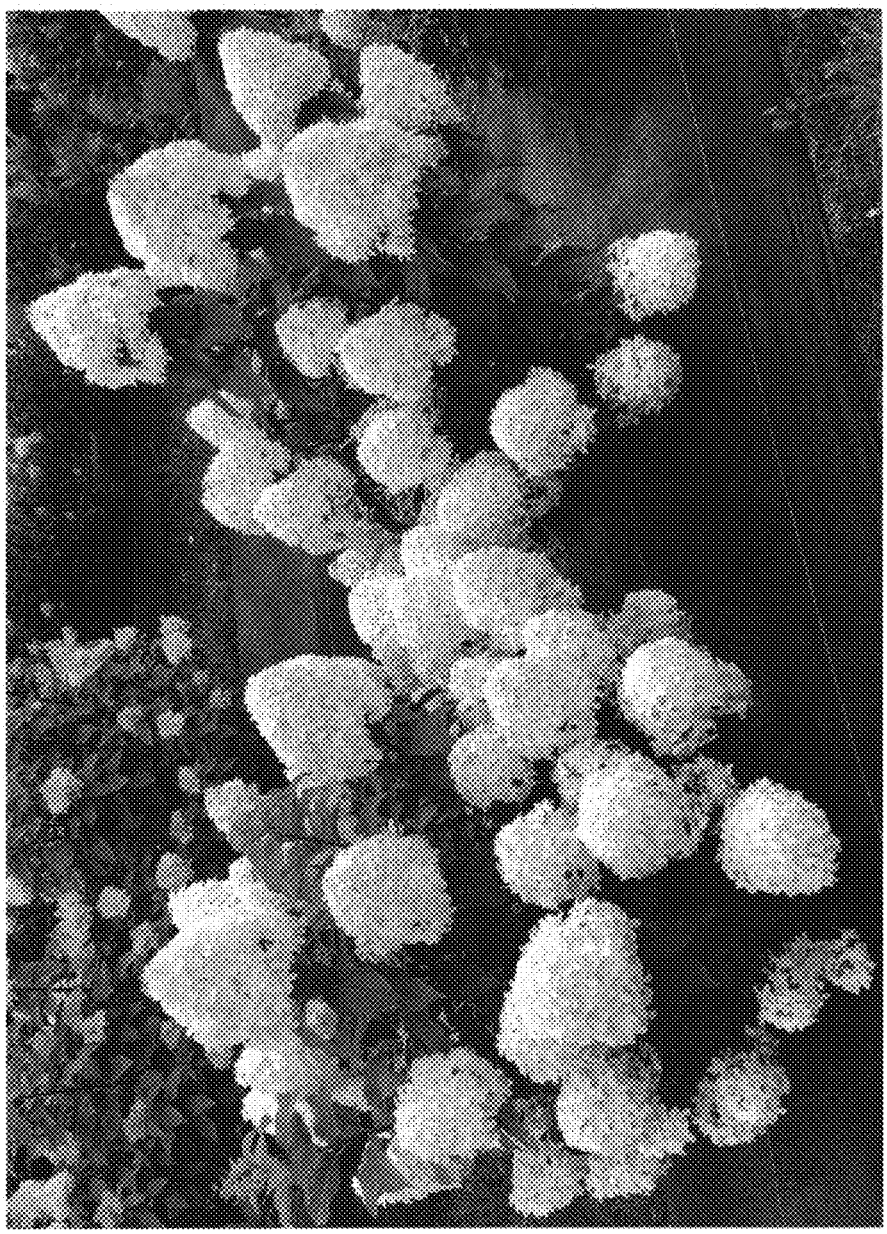
Figure 2:
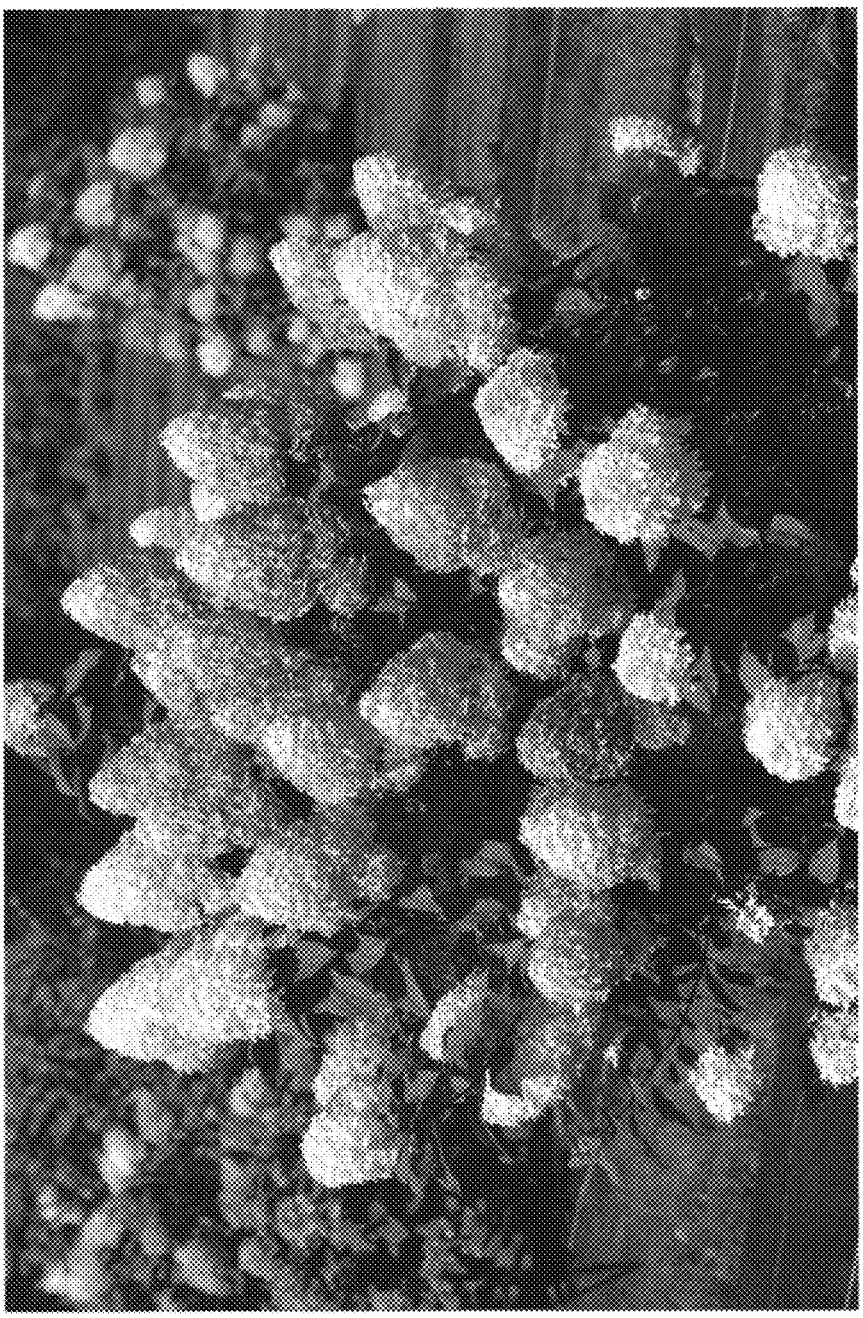
FIG. 2 illustrates in full color typical plants with more mature inflorescences.
Figure 3:
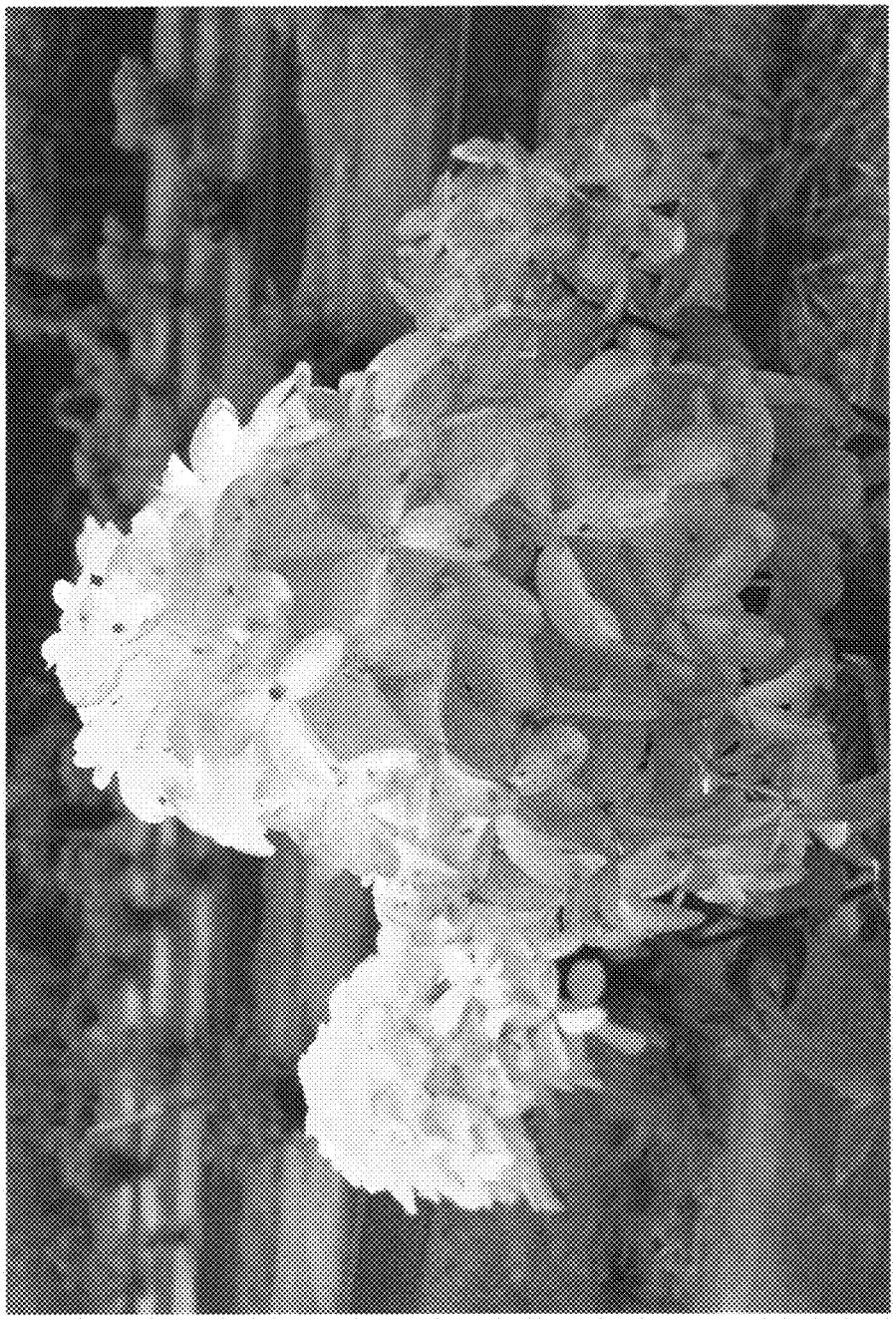
FIG. 3 illustrates an inflorescence with both mature and immature flowers.

Plants were grown outdoors, in Grand Haven, Mich. Age of the plant photographed is approximately 2 to 3 years. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Color Chart 2015 except where general terms of ordinary dictionary significance are used. The following observations and measurements describe 'SMNHPM' plants grown in a commercial poly greenhouse in Grand Haven, Mich. under natural lighting. Measurements were taken during Summer of 2019. The plants were about 4 years old planted in the ground. The growing temperature ranged from 5° C. to 27° C. Measurements and numerical values represent averages of typical plant types.

Botanical classification: *Hydrangea paniculata* 'SMNHPM'.

PROPAGATION

Time to initiate roots: Approximately 18 days.

Time to produce a rooted young plants: Approximately 60 days.

Root description: Fibrous, dense, freely branching, thick to thin roots. White to brown in color, not accurately measured with R.H.S. chart.

Propagation method: Softwood cuttings.

PLANT

Plant type: Flowering deciduous perennial shrub.

Age of plant described: Approximately 2 to 3 years old.

Growth habit: Upward and slightly outward.

Overall plant shape: Upright. Somewhat V-shaped.

Height: 60 cm.

Plant spread: 72 cm.

Plant vigor: Strong, and vigorous.

Branching habit: Upright and outward.

Length of primary lateral branches: 37 cm.

Diameter of lateral branches: 5 mm.

Quantity of lateral branches: About 50.

Stem:

*Stem shape.*—Rounded.

*Stem strength.*—Strong.

*Color.*—Immature: RHS Greyed-Orange 174A. Mature: Close to RHS Grey-Brown N200A.

*Pubescence.*—Yes, more prevalent on newer growth. Mature stems somewhat woody.

*Aspect.*—35 to 45°.

Internode length: 3.5 cm.

Lenticels: Moderate density. About 3 to 7 per linear cm of stem. About 1 mm wide and 2-4 mm long.

*Color.*—RHS Greyed-Orange 167B.

FOLIAGE

Leaf:

*Arrangement.*—Opposite.

*Leaf shape.*—Ovate.

*Average length.*—New: 4-5 cm. Mature: 6-10 cm.

*Average width.*—New: 2 cm. Mature: 3-5 cm.

*Apex.*—Acuminate.

*Base.*—Obtuse to Cuneate.

*Margin.*—Serrulate.

*Texture of top surface.*—Rough pubescence.

*Texture of bottom surface.*—Smooth, coriaceous, slightly pubescent.

*Leaf pubescence.*—Yes, both surfaces.

*Color.*—Young foliage upper side: RHS Yellow-Green 146B. Young foliage under side: RHS Yellow-Green 147B. Mature foliage upper side: RHS Green 137A. Mature foliage under side: RHS Yellow-Green 147B.

*Venation.*—Pattern: Pinnate. Color upper side: RHS Yellow-Green N144B. Color under side: RHS Yellow-Green 145D.

*Petiole.*—Average Length: 1 cm. Diameter: 2-3 mm. Petiole color upper side: RHS Yellow-Green 145A. Petiole color lower side: RHS Yellow-Green 145A. Petiole Texture upper side: Smooth, coriaceous, slightly pubescent. Petiole Texture lower side: Smooth, coriaceous, slightly pubescent.

FLOWER

Natural flowering season: Early Summer.

Inflorescence:

*Type.*—Mophead.

*Quantity of flowers per inflorescence.*—Fertile flowers: 50-100. Sterile flowers: About 200.

*Persistent or self-cleaning.*—Persistent, self-cleaning after several weeks.

*Longevity.*—Individual flowers stay fresh on the plant for about 2 weeks. Inflorescences are ornamental for several weeks. Fragrance: None detected.

Panicle:

*Shape.*—Panicle.

*Height.*—15 cm.

*Diameter.*—14 cm.

Sterile flower:

*Bud shape.*—Orbicular and lobed.

*Bud length.*—1.5 mm.

*Bud diameter.*—1.5 mm.

*Bud color.*—RHS Yellow-Green 145C.

*Flower length.*—About 2 mm.

*Flower diameter.*—About 2.5 mm.

Sterile flower petals: None.
Sterile flower sepal:
*Arrangement*.—Whorl.
*Number*.—4.
*Shape*.—Elliptic.
*Tip*.—Obtuse.
*Base*.—Rounded to slightly acute.
*Margin*.—Entire.
*Length*.—1-1.5 cm.
*Width*.—8-10 mm.
*Texture, upper*.—Smooth, soft.
*Texture, lower*.—Smooth, soft.
*Color*.—Upper surface at first opening: RHS Green-Yellow 1C. Under surface at first opening: RHS Green-Yellow 1D. Upper surface at maturity: RHS White 155C. Flushed, then turning Red-Purple 61C and N57A. Under surface at maturity: RHS White 155C. Flushed Red-Purple 61C. Turning N57C at maturity.
Sterile flower pedicel:
*Length*.—1.2 cm.
*Diameter*.—1 mm.
*Angle*.—45-90°.
*Strength*.—Moderate.
*Texture*.—Pubescent.
*Color*.—RHS White 155C.
Fertile flower:
*Bud shape*.—Orbicular and lobed.
*Bud length*.—3 mm.
*Bud diameter*.—4 mm.
*Bud color*.—RHS White NN155C with bit of Greyed-Purple 186C at the top.
*Flower shape*.—Star-shaped.
*Length*.—6 mm.
*Depth*.—5 mm.
*Flower aspect*.—Upright.
*Longevity*.—1 to 2 weeks.
Fertile flower petals:
*Arrangement*.—Whorl.
*Quantity*.—5.
*Length of petal*.—About 1 mm.
*Width of petal*.—1 mm.
*Apex*.—Acute.
*Shape of petal*.—Triangular.
*Petal margin*.—Entire.
*Petal base*.—Truncate.
*Petal texture*.—Smooth, upper and under side.
*Color*.—Upper surface at first opening: RHS White 155C. Under surface at first opening: RHS White 155C. Upper surface at maturity: RHS White 155C. Under surface at maturity: RHS White 155C.
Fertile flower sepal:
*Number*.—5.
*Arrangement*.—Ungulate.
*Shape*.—Fused/inconspicuous.
*Apex*.—Acute.
*Base*.—Rounded to obtuse.
*Margin*.—Entire.
*Length*.—1 mm.
*Width*.—2 mm.
*Texture*.—Smooth, glabrous, both sides.
*Color*.—Upper surface at first opening: RHS White 155C. Under surface at first opening: RHS White 155C. Upper surface at maturity: RHS White 155C. Under surface at maturity: RHS White 155C.
Fertile Flower Pedicel:
*Angle*.—Upright.
*Strength*.—Strong.
*Length*.—2 mm.
*Width*.—1 mm.
*Texture*.—Smooth.
*Color*.—RHS White 155A.

REPRODUCTIVE ORGANS

Sterile flowers: Reproductive organs not present.
Fertile flowers:
Stamens:
*Number*.—8.
*Filament length*.—0.75 mm.
*Filament color*.—RHS Yellow-Green 145A.
Anthers:
*Shape*.—Linear.
*Length*.—1 mm.
*Color*.—RHS Yellow-Green 145A.
*Pollen*.—Not observed.
Pistil:
*Number*.—1.
*Length*.—1 mm.
*Style*.—Length: 0.75 mm. Color: RHS Yellow-Green 145A. Ovary color: RHS White 155A and RHS Yellow-Green 145B.
*Stigma*.—Shape: Club. Color: RHS Yellow-Green 145A.

OTHER CHARACTERISTICS

Seeds and fruits: None observed.
Disease/pest resistance: Neither resistance nor susceptibility to normal diseases and pests of *Hydrangea* have been observed.
Temperature tolerance: USDA Zones 4 to 9.

What is claimed is:

1. A new and distinct cultivar of *Hydrangea* plant named 'SMNHPM' as herein illustrated and described.

* * * * *